United States Patent [19]
Graether

[11] Patent Number: 5,427,088
[45] Date of Patent: Jun. 27, 1995

[54] APPARATUS FOR INSERTING A PUPIL EXPANDER

[76] Inventor: John M. Graether, 611 Elmwood Dr., Marshalltown, Iowa 50158

[21] Appl. No.: 77,273

[22] Filed: Jun. 17, 1993

Related U.S. Application Data

[63] Continuation-in-part of Ser. No. 959,055, Oct. 9, 1992, Pat. No. 5,322,054, which is a continuation-in-part of Ser. No. 836,361, Feb. 18, 1992, Pat. No. 5,267,553.

[51] Int. Cl.⁶ .............................................. A61B 17/28
[52] U.S. Cl. ...................... 128/20; 606/107; 606/207
[58] Field of Search ............... 128/20, 3; 606/107, 606/205, 206, 207, 208; 30/159, 162

[56] References Cited

U.S. PATENT DOCUMENTS

| | | | |
|---|---|---|---|
| 459,818 | 9/1891 | Pearson et al. | 606/205 X |
| 1,105,641 | 8/1914 | Feaster. | |
| 2,147,800 | 2/1939 | Sadowski. | |
| 2,464,114 | 3/1949 | Bloecher. | |
| 2,584,547 | 2/1952 | Cahn | 606/206 X |
| 2,812,758 | 11/1957 | Blumenschein. | |
| 2,948,961 | 8/1960 | Ortner | 30/162 |
| 3,192,624 | 7/1965 | Gringer | 30/162 |
| 3,490,455 | 1/1970 | Illig. | |
| 3,807,393 | 4/1974 | McDonald. | |
| 4,037,589 | 7/1977 | McReynolds. | |
| 4,257,406 | 3/1981 | Schenk. | |
| 4,387,706 | 6/1983 | Glass. | |
| 4,452,235 | 6/1984 | Reynolds. | |
| 4,684,113 | 8/1987 | Douglas et al. . | |
| 4,782,820 | 11/1988 | Woods. | |
| 4,906,247 | 3/1990 | Fritch. | |
| 4,911,158 | 3/1990 | Weatherly. | |
| 4,991,567 | 2/1991 | McCuen, II et al. . | |
| 5,066,297 | 11/1991 | Cumming | 606/107 |
| 5,099,578 | 3/1992 | Jan | 30/162 |
| 5,163,419 | 11/1992 | Goldman. | |
| 5,176,686 | 1/1993 | Poley | 606/107 |
| 5,217,464 | 6/1993 | McDonald | 606/107 |
| 5,222,972 | 6/1993 | Hill et al. | 606/205 |
| 5,267,553 | 12/1993 | Graether | 128/20 |
| 5,284,162 | 2/1994 | Wilk | 606/205 |
| 5,308,357 | 5/1994 | Lichtman | 606/206 X |

Primary Examiner—Richard J. Apley
Assistant Examiner—Donna L. Maraglio
Attorney, Agent, or Firm—Zarley, McKee, Thomte, Voorhees & Seas

[57] ABSTRACT

A pupil expander insertion tool includes an elongated housing having a hollow chamber with a retractable blade extending through an aperture in the forward end of the housing and from the hollow chamber. The forward end of the retractable blade includes a pair of spaced-apart legs and a rearwardly extending slot therebetween, the slot adapted to receive a pupil expander in an elongated condition. The forward end of the housing includes a pair of forwardly projecting legs spaced above and parallel to the blade legs, to receive the tabs of a pupil expander between the housing legs and blade and the folded strap between the housing legs.

7 Claims, 3 Drawing Sheets

APPARATUS FOR INSERTING A PUPIL EXPANDER

CROSS REFERENCE TO RELATED APPLICATIONS

This application is a continuation-in-part of application Ser. No. 07/959,055 filed Oct. 9, 1992, which is now U.S. Pat. No. 5,322,054, which is a continuation-in-part of application Ser. No. 07/836,361 filed Feb. 18, 1992, which is now U.S. Pat. No. 5,267,553.

TECHNICAL FIELD

The present invention relates generally to apparatus utilized during eye surgery, and more particularly to an improved apparatus for the insertion of a pupil expander within the anterior chamber of the eye.

BACKGROUND OF THE INVENTION

The pupil expander of my issued U.S. Pat. No. 5,267,553 comprises a ring of silicone or other suitable soft plastic tubular material (e.g. Silastic ®silicone, Dow Corning, durometer value of about 80) with an outside diameter of 8.2 millimeters and an inside diameter of 7.0 millimeters. The ring has a C-shaped cross-sectional configuration with a peripheral opening at the outside edge. The ring is incomplete with approximately a 3.5 millimeter gap to permit surgical maneuvers within it, and that gap is bridged by a strap between the open ends of the ring. There are also two tabs with holes, which are used for manipulation of the device inside and outside the eye.

In operation, when it is desired to insert the pupil expander into the eye during a surgical procedure, the expander is first mounted on a carrier block or delivery case, as described in my co-pending patent application with said description being incorporated by reference herein. The pupil expander is then stretched into an elongated condition wherein the pupil expander is in a convenient position for removal and handling. My previous patent applications describe the use of forceps to manipulate the pupil expander.

The method of use of this pupil expander comprises the moving of the pupil expander, which is inserted into the anterior chamber of the eye through a previously prepared scleral or corneal incision. The expander is advanced across the anterior chamber until the flared end of the expander engages the iris at a 6 o'clock position. A spatula or lens manipulator is used to hold the expander in place against the iris sphincter while the forceps tips are partially withdrawn. The tips are then closed on the expander, and the tips are advanced into the eye causing the expander to enlarge horizontally engaging additional iris. The tips are then withdrawn an additional millimeter or two, and the above maneuver is repeated until the expander has been advanced onto the sphincter and the pupil has been gradually dilated. When the forceps have been withdrawn until they are opposite the tabs on the expander, the handle is lifted pushing the tips and the contained expander down toward the lens permitting the tabs to come down against the iris and completing the placement of the expander entirely within the pupil.

Because of the extremely small size of the pupil expander, the handling thereof is very delicate and sensitive, and ordinary forceps are not adapted for easily handling thereof.

It is therefore a principal object of the invention to provide apparatus for easily grasping and manipulating the pupil expander of my co-pending application to insert the expander in an eye without the need for a second instrument.

These and other objects will be apparent to those skilled in the art.

SUMMARY OF THE INVENTION

The pupil expander insertion tool of the present invention includes an elongated housing having a hollow chamber with a retractable blade extending through an aperture in the forward end of the housing and from the hollow chamber. The forward end of the retractable blade includes a pair of spaced-apart legs and a rearwardly extending slot therebetween, the slot adapted to receive a pupil expander in an elongated condition. The forward end of the housing includes a pair of forwardly projecting legs spaced above and parallel to the blade legs, to receive the tabs of a pupil expander between the housing legs and blade. The notch formed between the housing legs is adapted to receive the folded strap of an elongated pupil expander. The rearward portion of the retractable blade has an arch formed therein with a slidable actuator extending through a slot in the housing wall to engage the blade arch. An actuator plate located within the hollow chamber has corrugations on an upper surface which are biased into engagement with corrugations on the lower surface of the housing upper wall by the blade arch. An enlarged button on the upper end of the actuator permits manual movement of the actuator plate and blade by overcoming the biasing force of the arch and the biasing force produced by frictional contact between the corrugations of the actuator plate and housing upper wall. Uniform spacing of the corrugations provides predetermined selective slidable movement of the blade with respect to the housing.

DESCRIPTION OF THE PREFERRED EMBODIMENT

Figure 1:
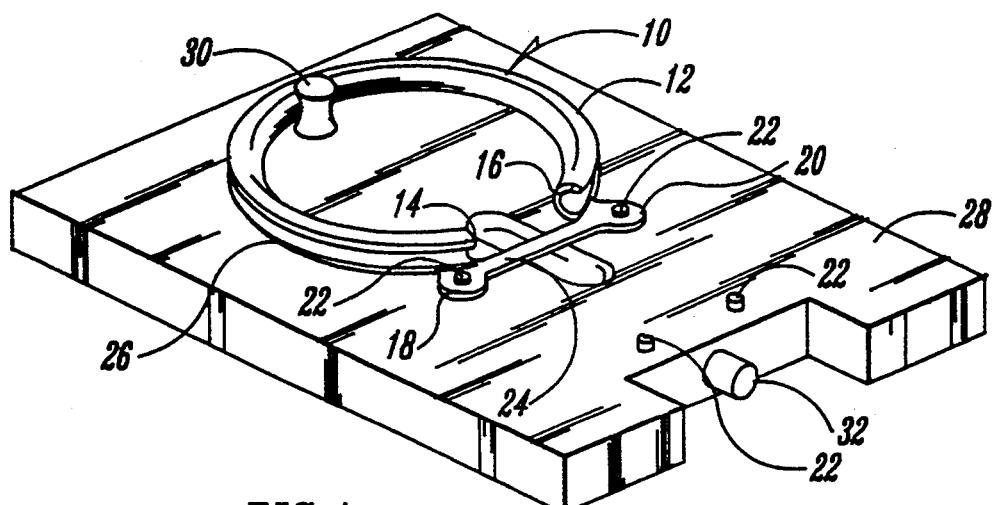
FIG. 1 is a perspective view of the carrier block of my co-pending application with the pupil expander of my co-pending application mounted thereon in its storage position.

Referring now to the drawings, and more particularly to FIG. 1, the pupil expander of the present invention is designated generally at 10, and includes a hollow ring member 12 which has opposite ends 14 and 16. Tabs 18 and 20 are formed adjacent ends 14 and 16, respectively, and each tab has an aperture 22 therein. A strap 24 extends between tabs 18 and 20 to hold ring member 12 in a circular configuration. Ring member 12 is generally C-shaped in cross-section and has an outer peripheral opening 26 which is adapted to engage the tissue of the eye as described in my issued U.S. Pat. No. 5,267,553, said description being herein incorporated by reference. Pupil expander 10 assumes a circular configuration when in its storage position on a carrier block 28 or delivery case.

Figure 2:
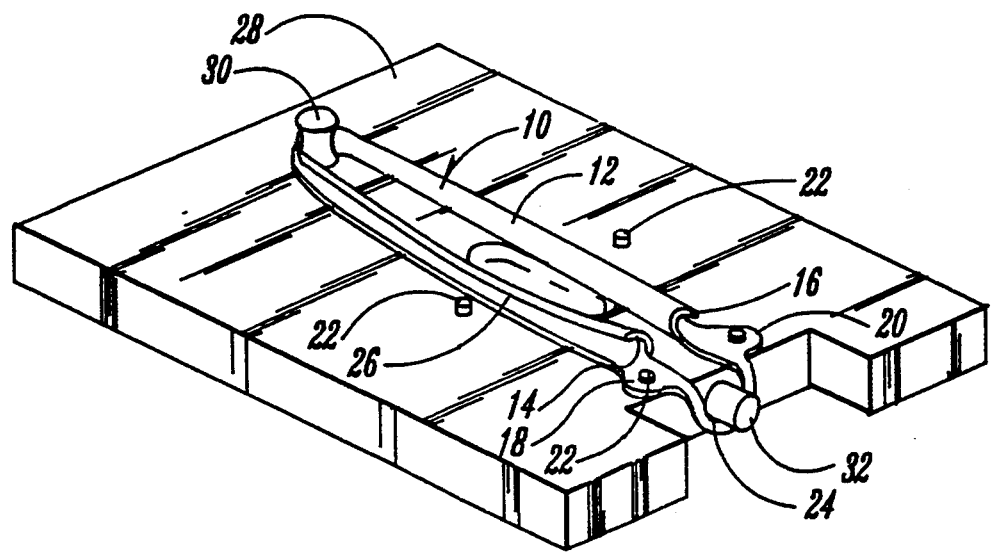
FIG. 2 is a perspective view similar to that of FIG. 4 but showing the pupil expander after is has been moved to its elongated position just prior to removal from the carrier.

Referring now to FIG. 2, pupil expander 10 is shown in an elongated configuration on carrier block 28 stretched between a first post 30 and a retention post 32, as described in my issued U.S. Pat. No. 5,322,054, said description being herein incorporated by reference. When stretched to the elongated condition of FIG. 2, the pupil expander 10 is in a convenient position for removal and handling by the insertion tool 40 of the present invention, shown in FIGS. 3-6.

Figure 3:
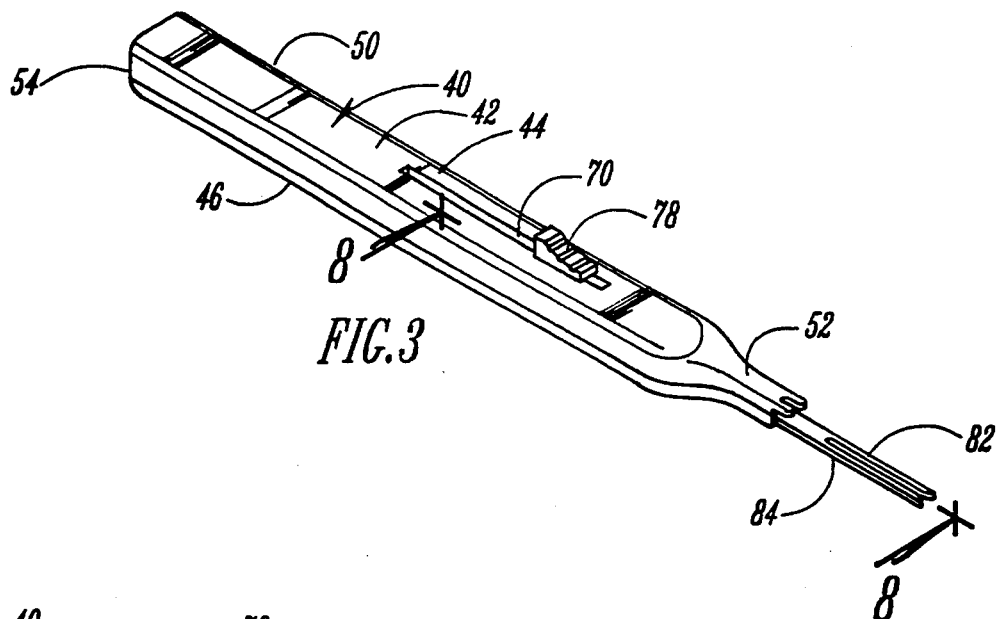
FIG. 3 is a perspective view of the insertion apparatus of the present invention for inserting a pupil expander within an eye.
Figure 4:
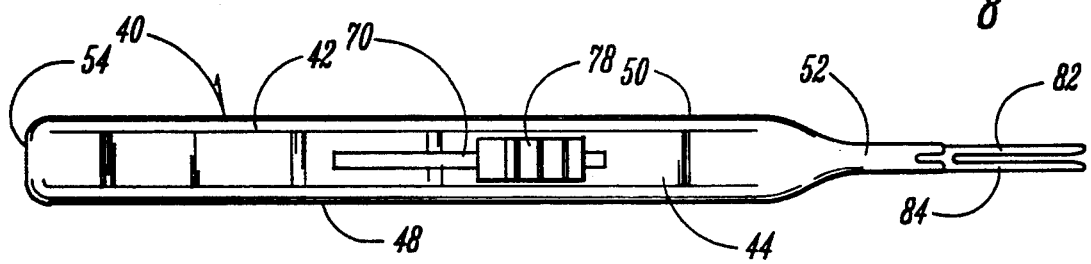
FIG. 4 is a plan view of the invention.
Figure 5:
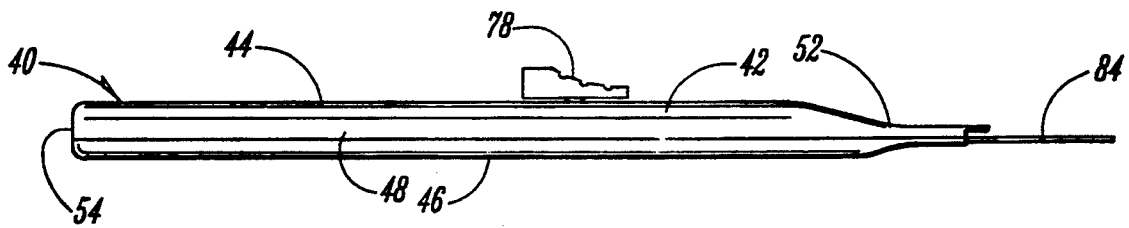
FIG. 5 is a side elevational view of the present invention.

Referring now to FIGS. 3-5, insertion tool 40 of the present invention includes an elongated housing 42 having an upper longitudinal wall 44, a lower wall 46, opposing side walls 48 and 50 and forward and rearward ends 52 and 54 respectively.

Figure 7:
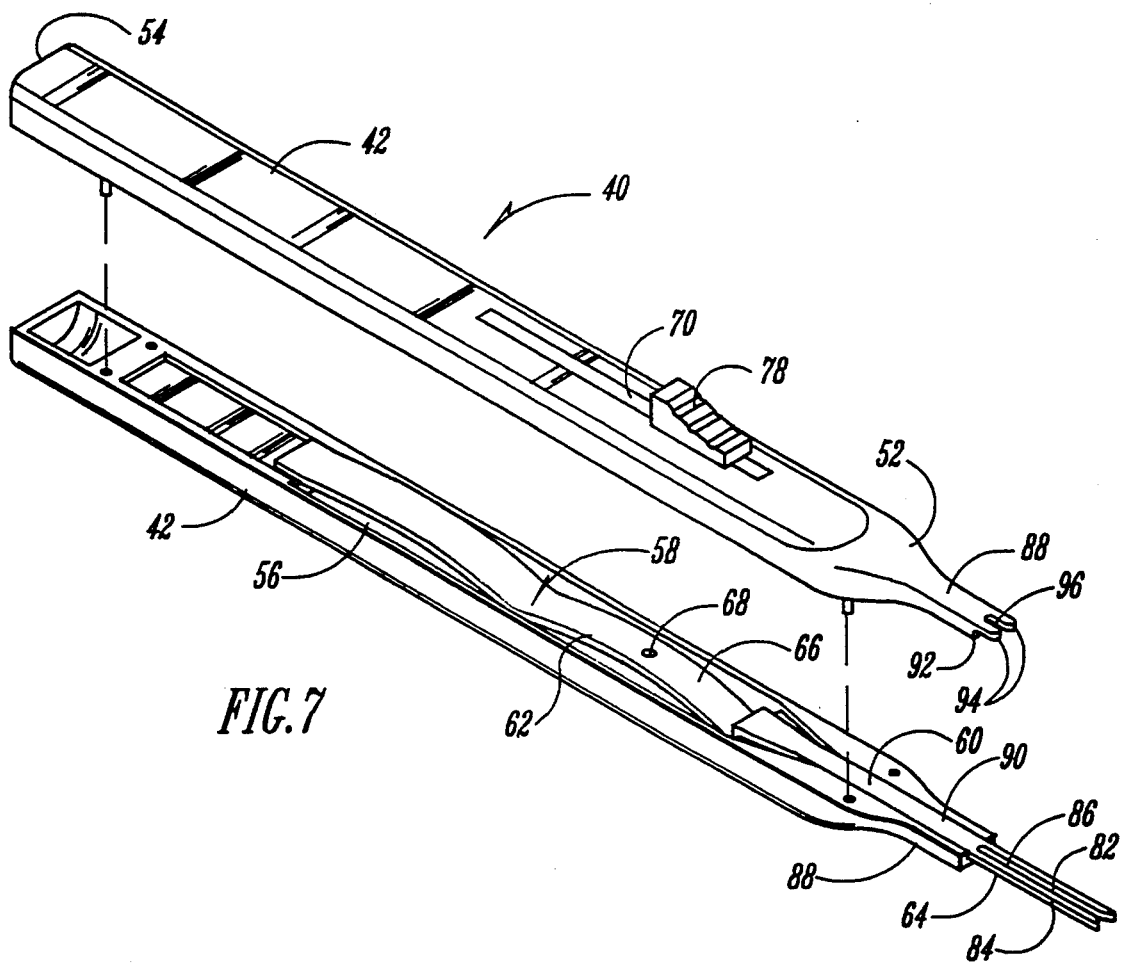
FIG. 7 is a perspective view similar to that of FIG. 3, but has the upper half of the apparatus exploded upwardly to show the interior of the invention.
Figure 8:
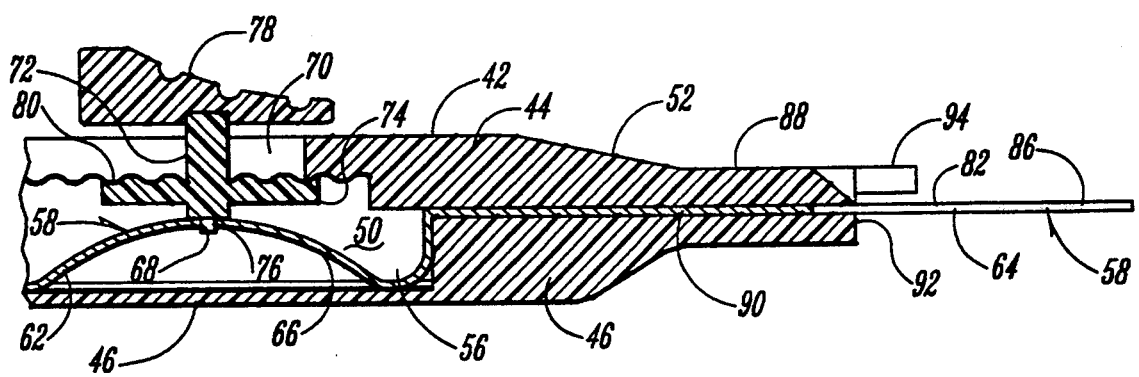
FIG. 8 is an enlarged sectional view taken at lines 8—8 in FIG. 3.

As shown in FIGS. 7 and 8, housing 42 has a hollow chamber 56 therein which retains a retractable blade 58, as described in more detail hereinbelow. Blade 58 is preferably formed from an elongated strip of 0.25 millimeter stainless steel, and includes a forward flat portion 60 and a rearward portion 62. Blade 58 is longitudinally slidable within hollow chamber 56, such that the forward tip portion 64 at the forward end of forward portion 60 may be extended outwardly of housing 42 and retracted within housing 42.

With reference to FIGS. 7 and 8, rearward portion 62 of blade 58 has a resilient arch 66 formed therein which vertically upwardly within hollow chamber 56. An aperture 68 is centered in the arch. A slot 70 is formed through upper wall 44, extending longitudinally directly over aperture 68 in arch 66. As shown in FIG. 8, slot 70 will receive a projecting pin 72 projecting upwardly from an actuator plate 74 which is operably mounted within chamber 56. Actuator plate 74 also includes a depending pin 76 engaged within aperture 68 of blade 58 so as to slide blade 58 longitudinally within hollow chamber 56. A button 78 mounted to the upper end of pin 72 exteriorly of housing 42, permits slidable movement of actuator plate 74 forwardly and rearwardly within hollow chamber 56.

Actuator plate 74 includes an upper surface having corrugations 80 formed therein. These corrugations correspond with corrugations formed in the lower surface of upper wall 44 of housing 42, to selectively retain blade 58 in its longitudinal position. As shown in FIG. 8, resilient arch 66 in blade 58 serves to bias actuator plate 74 into engagement with the corrugated lower surface of upper wall 44. Button 78 is mounted to pin 72 at a location spaced slightly above the upper wall 44 of housing 42, to permit the disengagement of the corrugations 80 from the corrugations of upper wall 44, by downward pressure on button 78 to overcome the bias of arch 66. Preferably, corrugations 80 are uniformly spaced approximately 1 millimeter apart, such that extension or retraction of blade 58 will occur in 1 millimeter increments.

Figure 9:
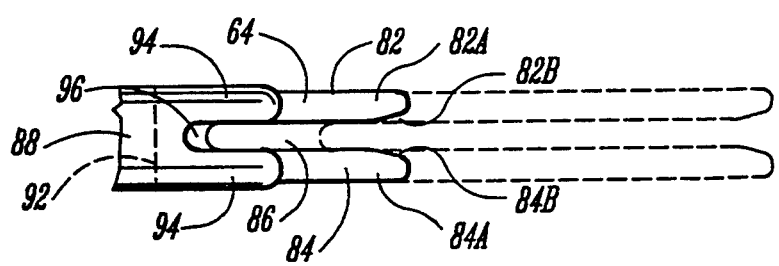
FIG. 9 is an enlarged scale plan view similar to that of FIG. 6, but showing the insertion blade in a partially retracted position, with the fully extended position of the blade shown in broken lines.

Forward tip portion 64 of blade 58 includes a pair of parallel spaced-apart legs 82 and 84 having forward ends 82a and 84a, respectively and forming a slot 86 therebetween. As shown in FIG. 9, leg tips 82a and 84a are beveled towards slot 86 and rounded towards the outer edges. These beveled surfaces 82b and 84b, respectively assist in guiding legs 82 and 84 into the peripheral opening 26 in pupil expander 10 (shown in FIG. 2). The length of slot 86 is long enough so as to hold a substantial portion of the length of pupil expander 10 when in the elongated condition shown in FIGS. 2 and 6.

Referring once again to FIG. 7, the forward end 52 of housing 42 narrows in height and width to form a forwardly projecting throat structure designated generally at 88. An aperture 90 formed in throat 88 extends from hollow chamber 56 and out the forward end of throat 88 such that tip portion 64 of blade 58 may extend and retract from housing 42.

Figure 6:
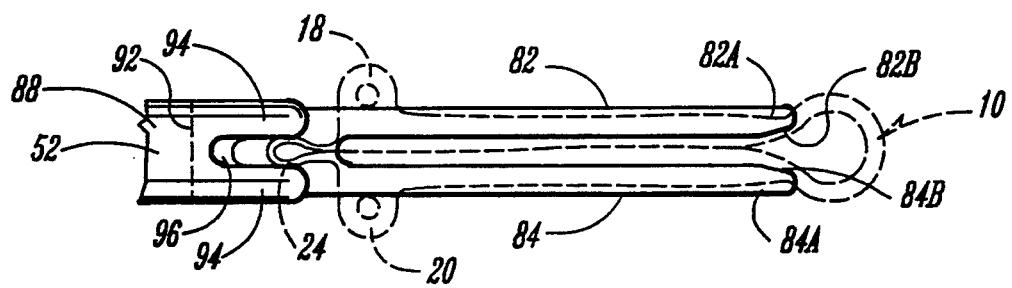
FIG. 6 is an enlarged scale plan view of the device of FIG. 4, with an elongated pupil expander of my co-pending application shown in broken lines thereon.

With reference to FIG. 8, the forward tip portion 64 of blade 58 projects from aperture 90 in the front vertical wall 92 of throat portion 88. As shown in FIG. 7, a pair of projecting legs 94 project forwardly from forward wall 92, and are spaced parallel and above blade 58. The notch 96 formed between legs 94 is designed to receive the folded strap 24 of pupil expander 10, as shown in FIG. 6. Legs 94 are spaced above aperture 90, as shown in FIG. 8, a distance sufficient to receive pupil expander tabs 18 and 20 between legs 94 and blade 58, as blade legs 82 and 84 are retracted (see also FIG. 6).

In operation, when it is desired to insert the pupil expander 10 into an eye during a surgical procedure, a pupil expander 10 is moved from the storage position (shown in FIG. 1) to an elongated condition, as shown in FIG. 2. The stretched elongated condition of FIG. 2 permits convenient removal and handling by insertion tool 40.

To load the pupil expander 10 onto insertion tool 40, forward tip portion 64 of blade 58 is first moved to the completely extended position shown in FIGS. 3-6, by pressing and sliding button 78 forwardly on housing 42. The tool is turned over and the forward ends 82a and 84a of blade legs 82 and 84 are moved longitudinally into the peripheral opening 26 of ring member 12, with beveled portions 82b and 84b assisting in sliding ring member 12 into slot 86 of forward tip portion 64 (see FIGS. 2 and 6). Folded strap 24 around post 32 is retained within notch 96 between projecting legs 94 on throat portion 88 of housing 42, as pupil expander 10 is removed from carrier block 28, so as to be configured as shown in FIG. 6. Once the pupil expander 10 is lifted from the carrier block 28, the tool is turned right side up and blade 58 is withdrawn 2 millimeters so as to bring tabs 18 and 20 under the projecting legs 94 and the strap 24 into notch 96. Thus, insertion tool 40 retains pupil expander 10 in its elongated condition for insertion into an eye in accordance with the procedures outlined in my co-pending applications.

Referring once again to FIG. 8, the retracting mechanism of insertion tool 40 is designed to allow the surgeon to retract blade 58 in 1 millimeter increments with relatively gentle pressure parallel to housing 42 to slide button 78. This is accomplished by providing generally rounded corrugations 80 on plate 74 and the lower surface of upper wall 44. If button 78 is pushed downward perpendicular to the handle, it will completely disengage plate 74 from upper wall 44 and allow the blade to be moved freely. The total movement of blade 58 must permit blade 58 to be completely withdrawn into housing 42 to permit proper insertion of pupil expander 10 within the eye. Preferably, housing 42 and button 78 are fabricated of an autoclavable material. To minimize the resistance encountered when blade 58 slides within aperture 90 of housing 42, it is desirable to highly polish at least forward portion 60 of blade 58.

Whereas the invention has been shown and described in connection with the preferred embodiment thereof, it will be understood that many modifications, substitutions and additions, such as pushing the expander off of a fixed blade, may be made which are within the intended broad scope of the appended claims. It is, therefore, seen that this invention will accomplish all of the stated objectives.

I claim:

1. A pupil expander insertion tool, comprising:
   an elongated housing having forward and rearward longitudinal ends, and a hollow chamber within said housing;
   a retractable blade means for holding a pupil expander in an elongated condition, operably mounted in said hollow chamber for longitudinal slidable movement;
   said housing having an aperture formed in the forward end thereof communicating with said hollow chamber;
   said retractable blade means including a forward portion and a rearward portion, the forward portion slidably journaled within said aperture for selective slidable movement between an extended position projecting forwardly from the forward end, and a retracted position within said aperture; and
   means connected to said forward portion for selectively sliding said blade means between the retracted and extended positions;
   said blade means further including a slot formed therein extending rearwardly from a forward end of said forward portion, forming a pair of forwardly projecting, parallel legs being spaced apart a predetermined distance and lying in a single plane, each of said legs having a blunt distal end, wherein the distance between said legs remains constant when said legs are moved between said retracted position and said extended position, and further wherein said legs remain in said plane when moved from said retracted position to said extended position.

2. The insertion tool of claim 1, further comprising a pair of parallel spaced-apart legs projecting forwardly from the forward end of said housing and spaced above said aperture such that the housing legs are parallel to and spaced above the blade means legs.

3. The insertion tool of claim 1, wherein said means for selectively sliding said blade means includes:
   a longitudinal slot formed in the upper wall of said housing located over the rearward portion of said blade means; and
   actuator means having upper and lower ends, the lower end engaging said blade means to slidably move the blade means, the upper end projecting through said slot upwardly and exteriorly of said housing.

4. The insertion tool of claim 3, wherein said actuator means includes an enlarged manually operable button on the upper end thereof located exteriorly of said housing.

5. The insertion tool of claim 3, wherein:
   said blade means is formed of a resilient material with memory;
   the blade means rearward portion has an upwardly projecting arch portion therein;
   the actuator means lower end engages said blade means on said arch portion, said arch portion being spaced above the lower wall of said housing;
   said actuator means includes an actuator plate located between said upper and lower ends within said hollow chamber, said actuator plate having an upper surface; and
   said arch portion extending upwardly a distance to bias the actuator plate upper surface into frictional contact with a lower surface of the upper wall.

6. The insertion tool of claim 5, further comprising a first set of corrugations formed on said actuator plate upper surface cooperable with a second set of corrugations formed on an upper wall lower surface of said housing, said first and second sets of corrugations adapted to resist longitudinal slidable movement of said actuator plate with respect to said housing upper wall.

7. The insertion tool of claim 6, wherein the corrugations within each of said first and second sets are uniformly spaced at predetermined distances, such that said blade means extends and retracts predetermined distances with slidable movement on the actuator plate.

* * * * *